(12) United States Patent
Zesiger

(10) Patent No.: US 6,743,397 B1
(45) Date of Patent: Jun. 1, 2004

(54) DEVICE FOR QUALIFYING PRODUCTS CONTAINING VOLATILE SUBSTANCES

(76) Inventor: Thierry Zesiger, Route du Brel 15, Hautfrive (CH), CH-2068

( * ) Notice: Subject to any disclaimer, the term of this patent is extended or adjusted under 35 U.S.C. 154(b) by 0 days.

(21) Appl. No.: 09/600,781

(22) PCT Filed: Jan. 19, 1999

(86) PCT No.: PCT/CH99/00024

§ 371 (c)(1),
(2), (4) Date: Aug. 21, 2000

(87) PCT Pub. No.: WO99/39175

PCT Pub. Date: Aug. 5, 1999

(30) Foreign Application Priority Data

Jan. 29, 1998 (FR) ............................................ 98 01191

(51) Int. Cl.[7] .................. G01N 21/00; G01N 31/00; G01N 33/00; G01N 1/10; G01N 25/20; G01N 1/00; B01L 3/02; G05B 21/00

(52) U.S. Cl. .................. 422/67; 422/63; 422/100; 422/80; 422/83; 700/266; 700/273; 700/274; 436/180; 436/174; 436/147

(58) Field of Search .................. 422/63, 67, 68.1, 422/100, 80, 83; 700/266, 273, 274; 436/180, 174, 147

(56) References Cited

U.S. PATENT DOCUMENTS

| | | | |
|---|---|---|---|
| 3,940,995 A | | 3/1976 | Harris et al. |
| 4,008,393 A | * | 2/1977 | Rapkin ........................ 436/59 |
| 4,604,363 A | * | 8/1986 | Newhouse et al. ......... 436/177 |
| 5,279,970 A | * | 1/1994 | Patashnick et al. ......... 436/133 |
| 5,472,669 A | * | 12/1995 | Miki et al. .................... 422/63 |
| 6,143,573 A | * | 11/2000 | Rao et al. .................... 436/180 |
| 6,335,202 B1 | * | 1/2002 | Lee et al. .................... 436/161 |
| 6,534,019 B1 | * | 3/2003 | Inoue .......................... 422/130 |
| 6,541,272 B1 | * | 4/2003 | Mitra .......................... 436/178 |
| 6,592,817 B1 | * | 7/2003 | Tsai et al. .................... 422/62 |
| 2002/0048818 A1 | * | 4/2002 | Sakairi et al. ............... 436/126 |
| 2002/0110490 A1 | * | 8/2002 | Sakairi et al. ............. 422/68.1 |

FOREIGN PATENT DOCUMENTS

| | | |
|---|---|---|
| EP | 0 451 566 | 10/1991 |
| EP | 0 770 869 | 5/1997 |
| JP | 08 201249 | 8/1996 |
| WO | 95 25268 | 9/1995 |
| WO | 96 01994 | 1/1996 |

* cited by examiner

*Primary Examiner*—Jill Warden
*Assistant Examiner*—Brian R Gordon
(74) *Attorney, Agent, or Firm*—Nixon & Vanderhye, P.C.

(57) ABSTRACT

The invention concerns a device for qualifying products containing volatile substances forming an analyte. The devices includes a measuring apparatus (2) provided with an enclosure (21a) and an electronic analyzing circuit (21b) for defining said analyte characteristics, a pumping system (30) for producing a vacuum inside said enclosure, a sampling chamber (16) wherein the analyte is introduced and a capillary (22) for connecting said chamber (16) to said enclosure (21a). The invention also has a chamber (16) that includes: a first inlet (18) for introducing the analyte and provided with a sealed plug (27, 60, 62); a second inlet (17) connected to a blow-down gas (11) and provided with a valve (23); and an outlet (19) for evacuating the gas contained in the chamber (16) and likewise provided with a valve (29), and it further has a transfer device (35, 32) for introducing the analyte into the chamber and a programmer (15) controlling the analyzing circuit (21b), the transfer device (35, 32) and the valves (23, 29), and arranged such that the purge of the chamber (16), the enclosure (21a) and the capillary (22) can be carried out automatically.

12 Claims, 6 Drawing Sheets

DEVICE FOR QUALIFYING PRODUCTS CONTAINING VOLATILE SUBSTANCES

The present application is a 371 U.S. National Phase of Application PCT/CH99/00024, filed Jan. 19, 1999.

The present invention relates to a device for qualification of products containing volatile substances forming an analyte, that comprises a measuring unit with a measuring enclosure and an electronic circuit for analysis to define the characteristics of the analyte, a pumping system to make a vacuum inside the enclosure, a sampling chamber in which the analyte is introduced and a capillary to connect the sampling chamber to the enclosure.

Such a device is particularly used to identify fragrant particles. That is why it is sometimes called "artificial nose". It finds applications in food or perfume industry for example and allows to ensure, by the analysis of fragrant molecules, that the quality of manufactured products stays in the limits of the required standard. It can be used particularly to highlight a modification of the characteristics of certain basic components or an evolution of one or another step of a manufacturing process.

To this effect, a defined quantity of product to control is sampled, in a programmed way, and confined in a vial with given dimensions, constant for a series of measurements. The vial is chosen to let a non filled space that contains the analyte, after having reached an equilibrium, made of volatile substances representative of the product.

In the devices actually used for such operations, the analyte is often characterized with a gas chromatograph. It is done by introducing the analyte in a chamber connected to a detection system with a column filled with particular material. The choice of that material and the operating conditions allow to induce different migration speeds for each substance making the analyte. A carrier gas, slightly pressurized, guarantees the carrying of these substances.

So the arrival time at the detector varies with the characteristics of the molecules making the analyte. Thus it is possible to know the quality of a product according to the sequence and the density of molecules arriving to the detector. However, the information obtained that way doesn't allow to identify the substances. It is generally enough to follow the evolution of the fingerprint left by the analyte after a measuring cycle.

To identify the substances, a mass or an infrared spectrometer has been added at the column outlet. Thus it is possible to have additional information on the chemical composition of the analyte.

The used mass spectrometer is generally chosen to be able to analyze the whole ion spectrum coming from the dissociation of the analyte molecules, that can have a molar mass up to 400 and more. Such spectrometers are expensive, delicate and sensitive to oxygen in its part responsible of the measurement, making them poorly adapted to the measurement of analytes commonly rich in air.

The Japanese patent 8'201'249 describes a device functioning without a chromatograph. It includes a chamber in which a sample is placed. This chamber is connected with a capillary to a mass spectrometer including a measuring enclosure. The chamber, the capillary and the enclosure are heated, not only to promote the odor release, but also to avoid their adsorption on the walls.

The use of the devices described above requires however some care, especially to ensure that the product previously measured doesn't remain in the chamber, the enclosure or the column, for example adsorbed on the walls, what could falsify the next measurement. Thus it is necessary to do some heavy and expensive operations to guarantee the cleanness of these devices.

SUMMARY OF THE INVENTION

The main purpose of the present invention is to palliate this drawback and more especially to allow the realization of a device such as defined above, easy to use and capable to be automated.

To that effect, the invention concerns a device to qualify products containing volatile substances forming together an analyte, that comprises a measuring unit with a measuring enclosure and an electronic circuit for analysis to define the characteristics of the analyte, a pumping system to make a vacuum inside the enclosure, a sampling chamber in which the analyte is introduced and a capillary to connect said chamber to said enclosure, the sampling chamber of this device including:
- a first inlet to introduce the analyte and fitted with a gastight cap,
- a second inlet connected to a source of purge gas and fitted with a valve and
- an outlet allowing the exhaust of the gas contained in the chamber and also fitted with a valve.

The device comprises moreover a transfer system to introduce the analyte into the sampling chamber and a command programmer for the analysis circuit, the transfer system and the valves, allowing to achieve sequentially the purge of the sampling chamber, the capillary and the enclosure, then the introduction of the analyte into the enclosure, and finally its analysis.

According to a first embodiment of the invention, the device is characterized by the fact that the programmer is set up in such a way that:
- in a first phase, the valves of the second inlet and the outlet are open to let the purge gas go through as long as a significant number of analyte particles previously analyzed may remain in the chamber, the enclosure or the capillary,
- in a second phase, the inlet valve is closed, preventing the penetration of the purge gas,
- in a third phase, the transfer system is activated, to introduce the analyte to measure into the chamber,
- in a fourth phase, the outlet valve is closed,
- in a fifth phase, at least, the analysis apparatus defines the characteristics of the analyte passing from the chamber into the encosure,
- in a sixth phase, the operation starts again at the first phase, as long as there are still other products to qualify.

According to another embodiment of the invention, the device comprises an adsorbing material on which the analyte is adsorbed.

In that case, preferably, the programmer is set up in such a way that:
- in a first phase, the valves of the second inlet and the outlet are open to let the purge gas go through as long as a significant number of analyte particles previously analyzed may remain in the chamber, the enclosure or the capillary,
- in a second phase, the inlet and outlet valves are closed quite simultaneously, preventing particularly the penetration of the purge gas,
- in a third phase, the transfer system is activated, to introduce the analyte to measure into the chamber,
- in a fourth phase, at least, the analysis apparatus defines the characteristics of the analyte passing from the chamber into the enclosure, and in a fifth phase, the operation starts again at the first phase, as long as there are still other products to qualify.

BRIEF DESCRIPTION OF THE DRAWINGS

Other characteristics and benefits of the invention will appear at the lecture of the following detailed description of a realization example given as an illustration and not limiting in connection with the annexed drawings in which:

the FIG. 1 represents a general view of a device according to the invention;

Figure 1:
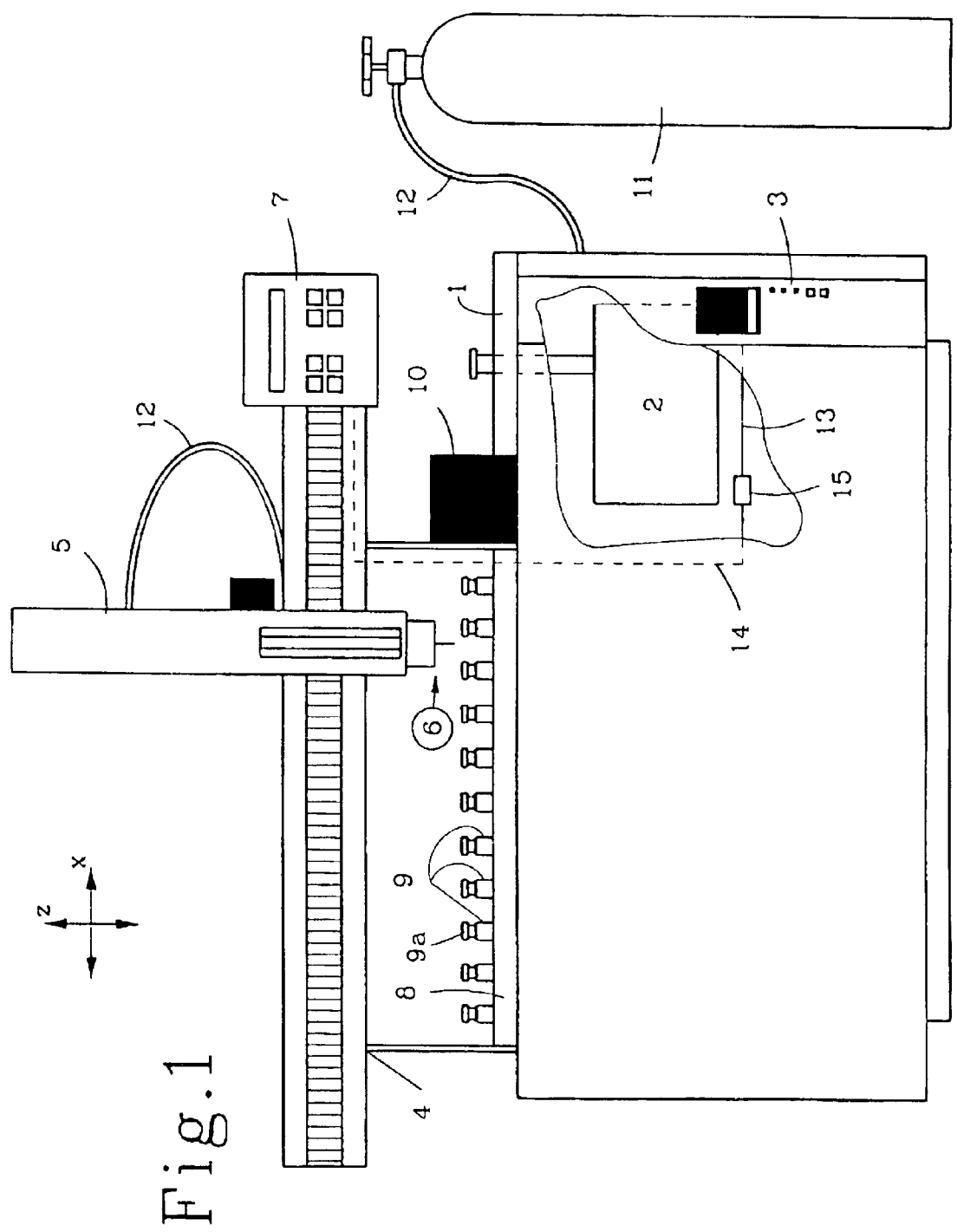
Figure 2:
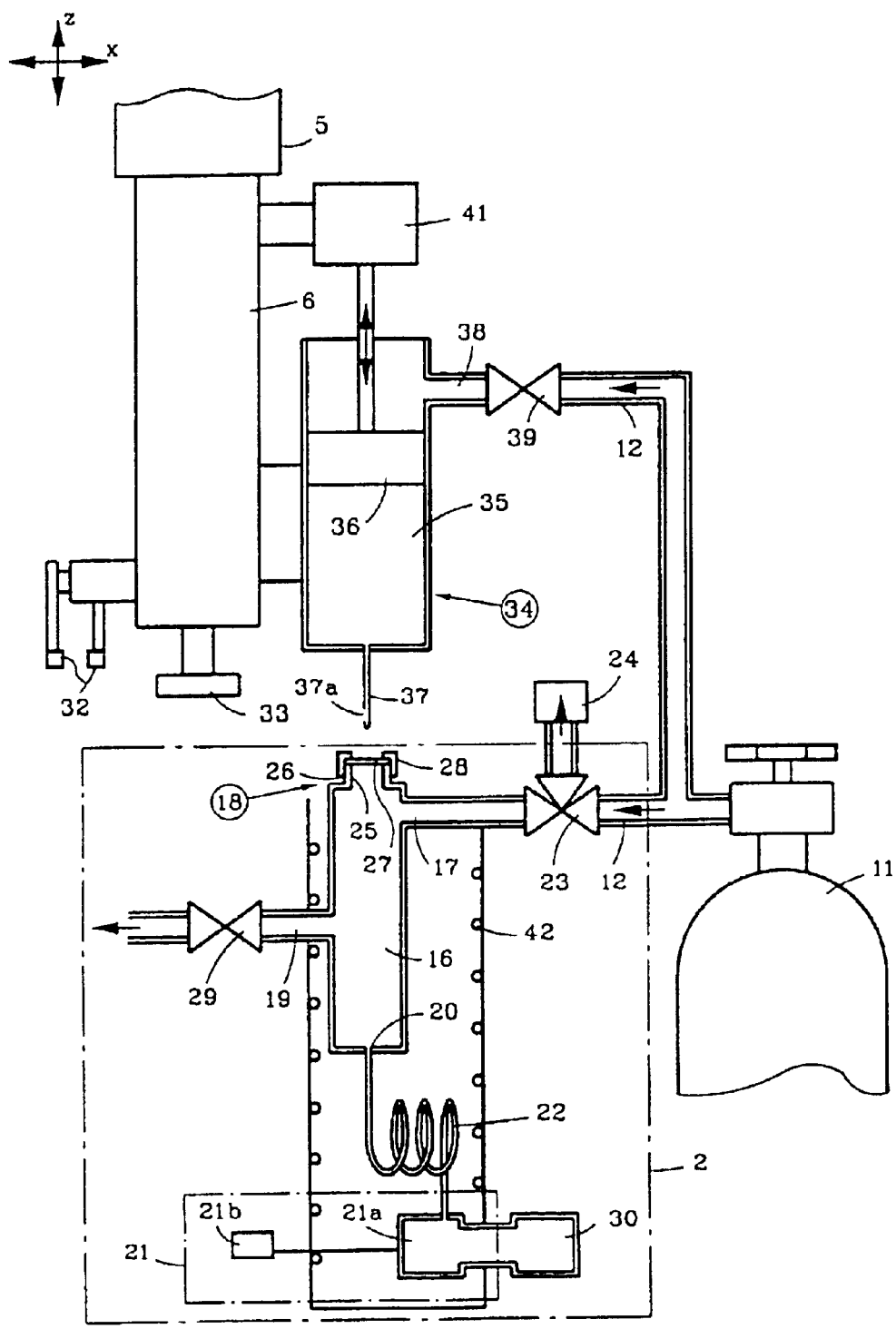
Figure 3A:
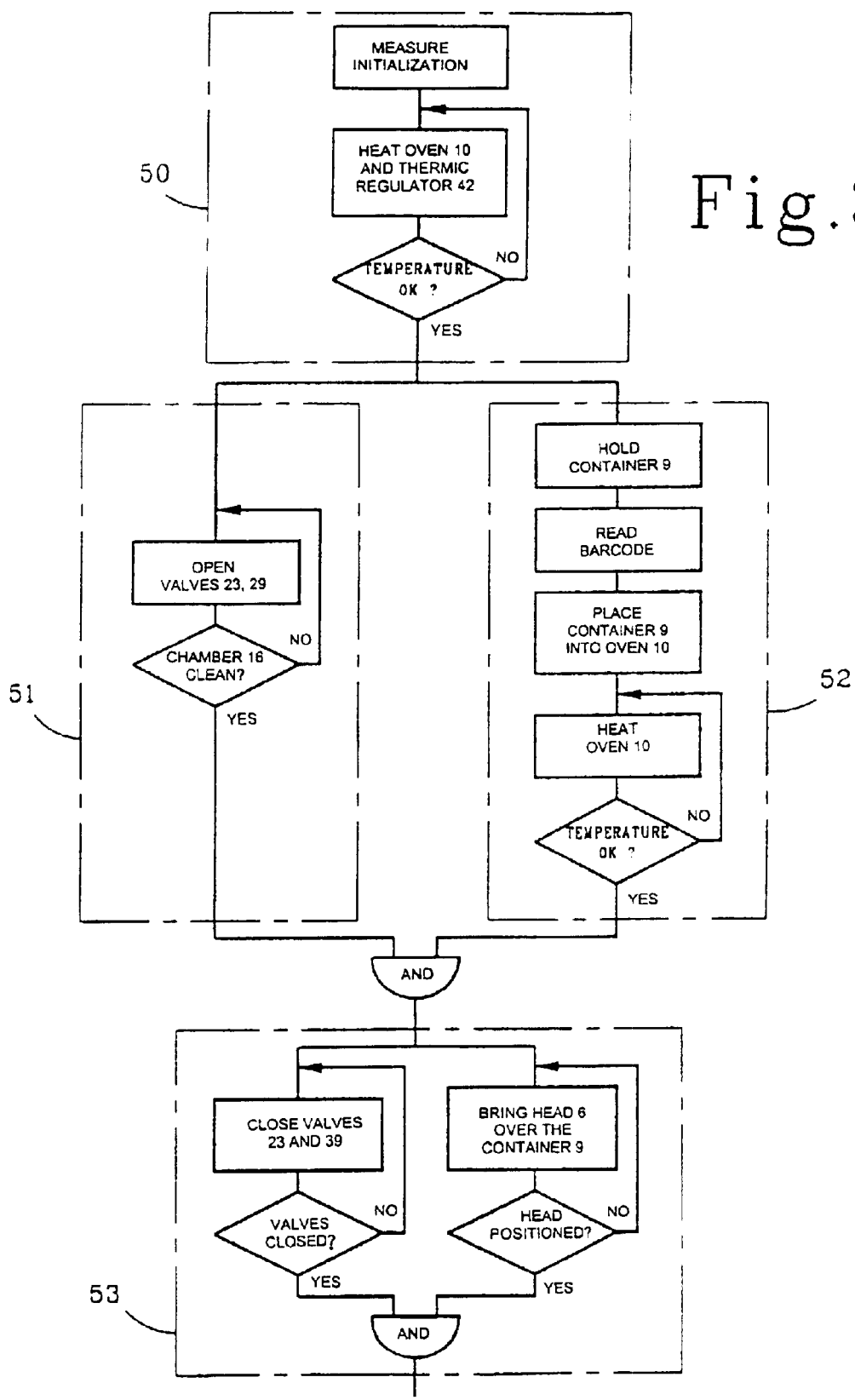
Figure 3B:
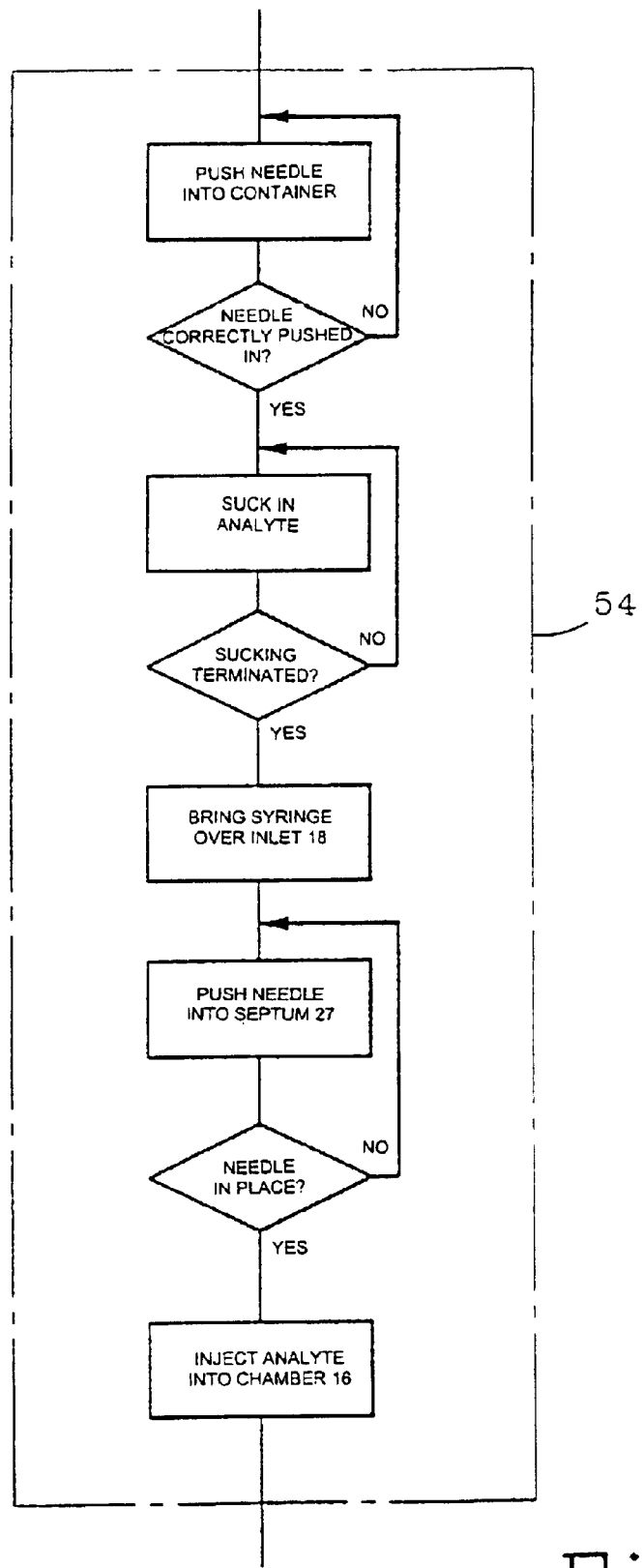
Figure 3C:
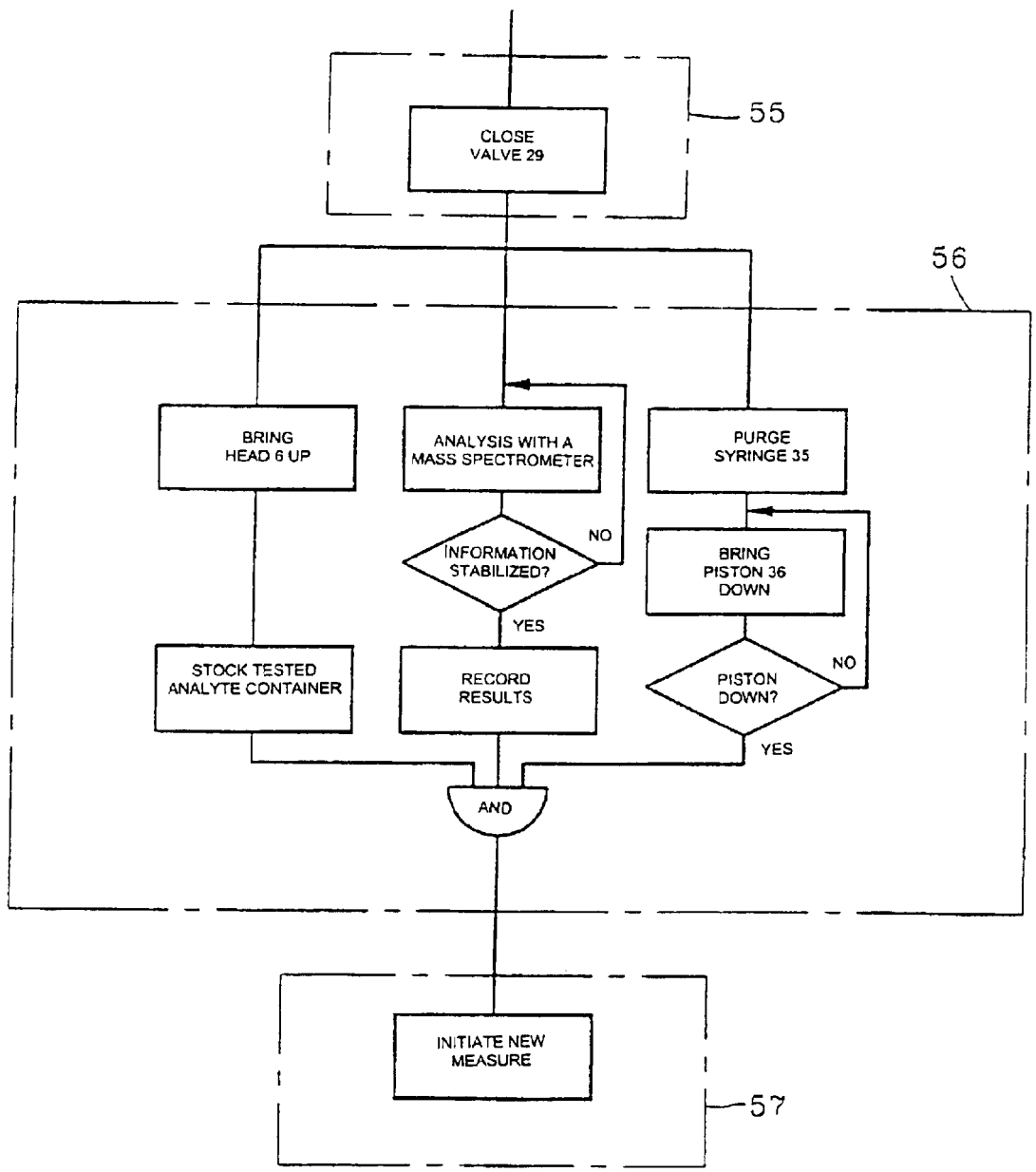
Figure 4:
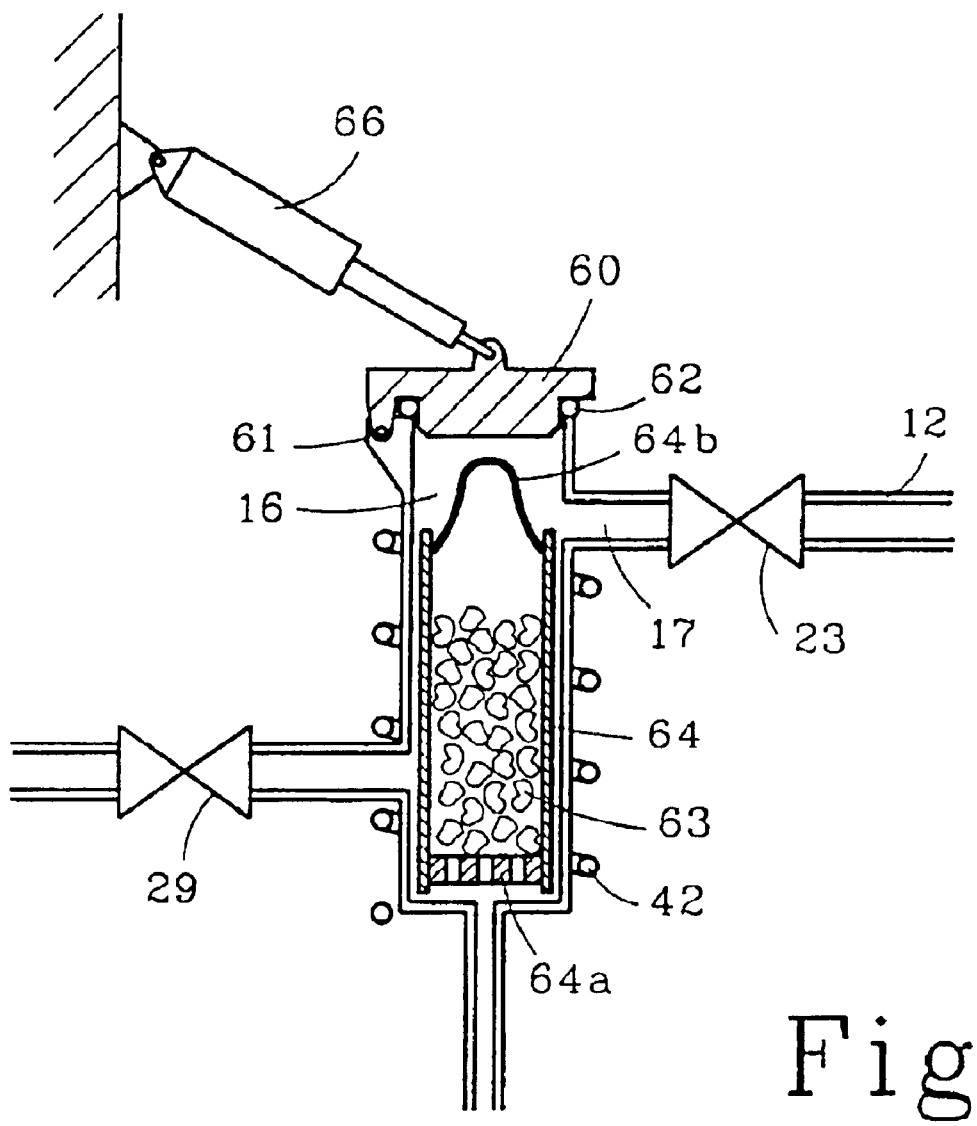

the FIG. 2 is a theoretical scheme showing with more details a part of the device of FIG. 1;

the FIG. 3 shows the logical functioning principle of a preferential command mode of the device according to the invention; and the FIG. 4 illustrates a variant of the embodiment represented in the FIG. 2.

DETAILED DESCRIPTION OF THE EMBODIMENTS

Referring now to the FIG. 1, it is observed that the device according to the invention comprises a parallelipipedic frame 1, in which a measuring apparatus 2 is placed, that will be described in more detail referring to the FIG. 2. A command panel 3 fills a part of one lateral face of the frame 1.

The upper face of the frame 1 is fitted with a rail 4, on which a moving bracket 5 slides according to an X axis, horizontal, and a Z axis, vertical. It has a manipulation head 6. A command box 7 fills one extremity of the rail 4.

The upper face of the frame 1 is fitted also with a tray holder 8, on which lay the vessels 9, as well as an oven 10, next to the tray holder 8.

The vessels 9 can be of different types, according to the product to analyze. However, in the following description, they will be considered as vials, closed with a gastight cap. It is composed of a septum and a ring 9a fixing the septum to the vial. The ring 9a is advantageously out of magnetic material.

A source of purge gas 11 supplies the analysis apparatus 2 and the head 6, with a tubing 12.

The command panel 3 and the command box 7 are connected respectively by the cables 13 and 14 to a programmer represented schematically in 15. The programmer 15 is advantageously realized with a computer that assumes the command of the different components of the device according to the invention, the measurement and the calculation of control and qualification parameters. For drawings simplification purpose, the connections between the programmer and the commanded components have not been represented.

The FIG. 2 allows to specify the way that the measuring apparatus 2 and the head 6 are designed. The measuring apparatus 2, whose different parts are circled by a mixed line, is commanded by the programmer 15. It comprises a sampling chamber 16 with two inlets 17 and 18 and two outlets 19 and 20. The sampling chamber 16 is connected to an analysis device 21 with a capillary 22 connected to the outlet 20. The temperature of the chamber 16, of the analysis device 21 and of the capillary 22 is kept at an adequate value with a temperature controller represented schematically in 42.

The first inlet 17 is controlled by a valve 23, commanded by the programmer 15, that can connect the chamber 16 to a vacuum pump represented schematically in 24, to the purge gas source 11 with the tubing 12, or that can also close the inlet 17.

The inlet 18 is defined by a cylinder portion 25, fitted with a thread 26. It is closed by a gastight cap composed of a septum 27 fixed on the extremity of the cylinder portion 25 with a ring 28 screwed on the thread 26.

The outlet 19 is meant to let the purge gas go out. It is composed of a valve 29, commanded by the programmer 15.

The analysis device 21 is advantageously composed of a mass spectrometer, for example the model sold under the trade-mark "Thermostar" by the company Balzers Instruments AG. It comprises an enclosure 21a and an electronic circuit for analysis 21b. The enclosure 21a is kept under vacuum with a pumping system, represented schematically in 30 and next to the enclosure 21a. The analysis circuit 21b measures the ionic currents for different masses and sends to the programmer 15 the collected information.

Such spectrometers allow to characterize ions whose molar mass can reach 300. That kind of spectrometer was used up to now only for gas and air analysis, it is far less sensitive to oxygen than the spectrometers allowing to measure ions with a molar mass equal to or higher than 400, such as the ones used up to now and associated to chromatographs.

The device operator can, with the command panel 3, define the masses that will be considered during the analyte qualification.

In a variant, the pump 24 can be suppressed. The chamber 16 is then connected directly to the pumping system 30.

The head 6 is mounted rigidly on the bracket 5. It comprises a pick-up device 32, a reader 33 and an analyte transfer device 34.

The pick-up device 32 is advantageously realized with an electromagnet cooperating with the ring 9a of the vials 9 or with pliers able to seize them by pressing. It is commanded by the programmer 15. Such devices are perfectly known by the professional. Thus they won't be described in a more detailed way.

The reader 33 allows to identify the vials 9, before they are gripped by pick-up device 32. This identification can be made advantageously with a bar-code borne by each vial 9. The collected information is sent to the programmer 15 to assume the identification of the measured products.

The analyte transfer device 34 comprises a syringe 35 fitted with a plunger 36 and a needle 37. The syringe 35 also has an inlet 38 fitted with a valve 39 commanded by the programmer 15 and connected with the tubing 12 to the gas source 11 used to purge it. It can also be advantageously heated, by standard means, not represented, to avoid a condensation or an adsorption of some analyte substances.

The plunger 36 is actuated with an electric motor represented schematically in 41 commanded by the programmer 15.

The needle 37 is fitted with a lateral aperture 37a, in its part near the tip. The functioning principle of the device described above is the following:

The products to control are contained in the vials 9, for example during the fabrication process, manually or automatically. The vials 9 are filled in order to keep a space between the product and the cap. They are put on the table 8 by manual or automatic means (not represented, because they don't belong directly to the invention). Each vial 9 bears advantageously identification means, such as a bar-code.

When the operator initializes a measurement, he sets the temperature of the oven 10 according to the product to control and to the volatile substances that the analyte must contain, generally ranging from 30 to 200 degrees centigrade. He chooses also which masses will be quantified by the spectrometer to define a fingerprint of the analyte. He specifies moreover the temperature of the chamber 16, the enclosure 21a, the capillary 22 and the syringe 35. These temperatures are preferably chosen slightly higher than that of the oven 10, in order to avoid the adsorption of little volatile substances on the walls of the chamber 16, on the capillary 22 and on the enclosure 21a. All values are entered in the programmer 15.

When the temperature is reached, the programmer 15 give the order to the bracket 5 to bring the head 6 over one vial 9 whose contents must be controlled. The head 6 seizes the vial 9 with the pick-up device 32 and put it in the oven 10.

The vial 9 stays there during a time long enough to let pass in the gaseous phase all substances necessary to form the analyte. This time is generally set between one and ten minutes. It can reach sometimes one hour. Simultaneously, the vial 9 can be slightly agitated, to promote the evaporation of the substances making the analyte and guarantee the homogeneity of the product and the analyte.

The dwell time in the oven 10 and its temperature vary according to the product and the analyte. The conditions of the dwell in the oven are set during preliminary tests, defining optimal conditions, able to assume an equilibrium between the analyte in gaseous phase and the product sample. These conditions are then kept constant in time to guarantee the reproducibility of the tests.

The programmer 15 commands also the heating and the purge of the measuring apparatus 2 and the transfer system 34. The purge is achieved with the purge gas contained in the bottle 11. The heating of the measuring apparatus is achieved with the controlled heater 42.

When the programmer 15 finds that the chamber 16, the enclosure 21a and the capillary 22 are clean, that the temperature of the apparatus 2 and the product contained in the vial 9 are at the adequate temperature, the head 6 places the transfer system 34 over the vial 9 staying in the oven 10. The motor 41 leads the plunger 36 in its sunken position in the syringe 35.

Then the head 6 lowers in such a way that the needle 37 pierces the septum of the vial 9 and stops in the free space. The motor 41 commands then the plunger 36 to move upwards, to transfer a part of the analyte from the vial 9 to the syringe 35.

The head 6 is then moved upwards, taking with it the needle 37 that leaves the vial 9. It is brought over the inlet 18 of the measuring apparatus 2.

Note that the pressure in the free space of the vial 9 is slightly higher than the atmospheric pressure, due to the heating of the product in the oven 10, that induces the volatilization of substances and the dilatation of the air confined in it. So, the pressure inside the syringe 35 is high enough to keep external air from penetrating in it during the moving.

The head 6 is lowered one more time. The needle 37 pierces the septum 27. The motor 41 commands the plunger 36 that injects the analyte into the chamber 16.

During this operation, the valve 23 is closed while the valve 29 is open. So, the pressure inside the chamber 16 remains nearby the external pressure, the purge gas still in the chamber 16 being ejected through the valve 29.

At the end of the injection, the valve 29 is closed.

As a variant, when the purge is finished and before the analyte is introduced, the chamber 16 can be emptied of the purge gas with the vacuum pump 24. During this operation, and during the analyte introduction into the chamber 16, the valve 29 is then closed.

Instead of purging the chamber 16, it is also possible to clean it by disposing of its contents, by pumping, with the vacuum pump 24.

After introduction of the analyte in the chamber 16, a part is sucked up towards the enclosure 21a under the effect of the pressure difference due to the fact that the enclosure 21a is kept under high vacuum by the pumping system 30.

The analyte molecules intended for the measurement are fragmented in ions that are analyzed in the enclosure 21a with the mass spectrometer. When an adequate amount of the analyte has penetrated into the enclosure 21a to guarantee the measurement precision, the collected information defined by the analysis circuit 21b are treated by the programmer 15.

More precisely, the programmer 15 records the ionic current for different mass values, selected beforehand, and compares this result with the values previously obtained for this type of analyte. The measuring time can be chosen for each mass, so that the quantity of current measured is enough to qualify optimally the product. In fact, some ions, although present in little quantities, are particularly significant. An increase of the measuring time allows then to increase the precision.

In other words, the fingerprint of the controlled analyte is defined and compared with a reference fingerprint, obtained by previous measurements.

If the obtained result is not satisfactory, the programmer 15 can be set to inform the operator of the recorded divergence, or even act directly on the production chain to change the working conditions.

A new measuring cycle can then be initiated, after the vial contained in the oven 10 has been removed and put back in an adequate place on the table 8, for example in the place it occupied before, to be either recycled or disposed of.

The programmer 15 is able to work according to two main modes. In the first mode, the functioning of the device according to the invention is controlled by bondage, while in the second mode it is controlled by programming.

The functioning scheme of the FIG. 3, that will be described hereafter, represents a functioning example by bondage. The description of this figure will be completed by specifying in what way a programming command is different. The operations of each different step are grouped in a rectangle with a mixed line.

As soon as the measurement has been initialized, which is represented by the rectangle 50, the programmer 15 commands the heating of the oven 10 and of the thermal controller 42.

When the temperatures are stabilized, the programmer 15 can start a first measuring cycle and makes, in a first time, the whole operations set listed in the rectangle 51. It commands first the opening of the valve 23, to assure the purge gas inlet into the chamber 16. It opens moreover the valve 29 to let the purge gas go out. Regarding the syringe 35, it is clean. The plunger 36 is located in the bottom of the syringe 35.

As long as the signal coming from the analysis circuit 21b to the programmer 15 shows the presence of substances different from the purge gas, the purge operation continues.

In the case of a second mode command, a purge time is entered in the programmer 15, defined beforehand, according to analyte previously measured.

In parallel, the programmer 15 sends orders to the driving device of the bracket 5 and the head 6, represented in the rectangle 52, which leads the pick-up device to go over a vial 9 containing the product to qualify, then to seize it and bring it into the oven 10. During this transfer, the bar-code reader 33 determines the contents of the vial 9 and transmits it to the programmer 15.

When the programmer 15 considers that the vial has the adequate temperature and that the chamber 16, the capillary 22 and the measuring enclosure 21a are clean, it commands a set of actions, corresponding to a second time and grouped in the rectangle 53 of the FIG. 3.

More precisely, the programmer 15 closes the valves 23 and 39 and gives the order to the bracket 5 to bring the head 6 over the vial 9, and especially the needle over its septum.

The programmer 15 checks then that the valves 23 and 39 are closed and that the head 6 is in an adequate position. This checking can be achieved with sensors cooperating respectively with the plunger 35, the valves 23 and 29 and the head 6.

When those conditions are fulfilled, the programmer 15 sends a series of orders corresponding to a third time and represented in the rectangle 54. The bracket 5 is moved vertically to lower the head 6 enough to let the needle 37 pierce the septum of the vial 9 and positions itself in the free space containing the analyte, without plunging in the product.

After the checking of this operation, the programmer 15 switches on the motor 41 to pull up the plunger 36 upwards, A calibrated dose of the analyte is then transferred from the vial 9 to the syringe 35.

When the programmer 15 finds that the amount of analyte is enough, it stops the motor 41 and the head 6 is lifted up, to free the needle 37 from the vial 9. The programmer 15 gives then the order to move the head 6 over the inlet 18. So the needle 37 finds itself over the septum 27 closing that inlet 18. The programmer 15 initiates then the lowering of the head 6. The needle 37 pierces the septum 27 and penetrates into the chamber 16.

The programmer 15 having checked that the needle 37 is in an adequate position, it gives the order to the motor 41 to sink the plunger 36 into the syringe 35, thus injecting the analyte into the chamber 16. To avoid a pressurization in the latter, the valve 29 has been kept open. So, the analyte sends the purge gas away from the chamber 16.

In a fourth time, represented by the rectangle 55, a sensor not represented in 10 the drawing, placed in the chamber 16, defines the moment when the pressure in it is adequate. The programmer 15 closes then the valve 29. As a variant, the pressure in the chamber 16 can be set as equal to the atmospheric pressure. In that case, it is enough that the valve 29 is formed by a valve allowing the evolving of a gas out of the chamber 16 to the outside, but preventing a penetration. Thus the chamber 16 can't be contaminated by substances coming from the apparatus surroundings. So, the valve 29 closes automatically.

In a fifth time, represented by the rectangle 56, the programmer 15 gives the order to the bracket 5 to lift up the head 6, thus taking the needle 37 out of the measuring apparatus 2. The vial 9, whose analyte is being analyzed, is removed from the oven 10 and placed in reserve. It can simply go back again to the place it occupied initially on the table 8.

The syringe 35 and the needle 37 are purged. To do this, the plunger 36 is lifted up over the aperture 38. The programmer 15 opens the valve 39. So, the purge gas goes through the syringe 35 and exits by the aperture 37a of the needle 37. The purge achieved this way can advantageously be completed by a back and forth movement of the plunger 36, that sends the purge gas away from the syringe 35.

In parallel, the programmer 15 analyzes the results given by the mass spectrometer, trough the analysis circuit 21b. When the given information is stabilized, the programmer 15 deals with them and puts them in memory. If necessary, it can be programmed in such a way that an alarm is switched on if the results don't agree with the defined norm. It is also possible to consider a direct setting of the fabrication process, based on the results obtained.

When those operations are finished, he programmer 15 can, in a sixth time represented by the rectangle 57, initiate a new measurement cycle, according to the same procedure as that described above.

In a variant represented in the FIG. 4, the analyte is no more introduced in the chamber 16 with a syringe, but fixed on an adsorbent.

Before this introduction, the adsorbent is placed, in adequate conditions of temperature, pressure and humidity, in an atmosphere containing the analyte or in which the analyte is circulating.

In that embodiment, the chamber 16 is closed by a lid 60 attached to the wall of the chamber 16 by a hinge 61. A seam 62 assures the tightness between the lid 60 and the wall of the chamber 16.

The analyte is transferred with a substrate 63, active carbon for example, contained in a cylindrical cup 64, which lower extremity is closed by a pierced wall 64a. The cup 64 is fitted moreover with a loop 64b allowing its handling.

The temperature controller 42 assures the heating of the chamber 16.

Before the introduction of the cup 64, the programmer 15 commands the closing of the valves 23 and 29 and the opening of the lid 60, through a motorized bracket 66, for example an air actuated piston, the pick-up device 32 brings then the cup 64 in the chamber 16. The programmer 15 commands the closing of the lid 60.

The temperature existing in the chamber 16 is chosen in a way to release the analyte. The programmer 15 commands the opening of the valve 23. So, the purge gas, introduced from the top into the chamber 16, assumes the role of a piston and pushes the analyte in the lower part of the chamber 16, helping thus its introduction into the capillary 22. The measurement is then achieved as it was described above.

When the measurement operation is finished, the cup 64 is removed with the adsorbent before the installation is purged.

This embodiment offers the same advantages as the solution previously described, and is well adapted to the analysis of substances present in traces and easy to desorb.

As it was noted through the previous description, the device according to the invention can assure an automated or semi-automated quality control of the products containing volatile substances, like those of the food industry. It demands a measuring equipment quite cheap, considering the given results. The precision obtained guarantees secure and repetitive tests.

Thus the background has shown that, although it has been given up to use a gas-phase chromatograph associated or not to a mass spectrometer allowing the measurement of ions having a molar mass higher than 300, the analyte fingerprint is altogether enough to assure the control of a production. Moreover, the measuring frequency of a device such as it has just been described is especially high. Thus a full measurement cycle can be achieved in a time defined practically by the time needed to heat the product to qualify.

What is claimed is:

1. Device to qualify products containing volatile substances forming together an analyte, comprising a measuring apparatus (2) with a measuring enclosure (21a) and an analysis electronic circuit (21b) to define the characteristics of said analyte, a pumping system (30) to make a vacuum inside said enclosure (21a), a sampling chamber (16) into which said analyte is introduced and a capillary (22) to connect said chamber (16) to said enclosure (21a), said chamber (16) comprising:

a first inlet (18) to introduce said analyte and fitted with a gastight cap (27; 60, 62), a second inlet (17) connected to a source of purge gas (11) and fitted with a valve (23), and, an outlet (19) allowing the exhaust of the gas contained in said chamber (16) and also fitted with a valve (29), the device comprising furthermore a transfer system (35, 32, 63, 64) to introduce the analyte into the sampling chamber, and a command programmer (15) for the analysis circuit (21b), for the transfer system (35, 32, 63, 64) and those valves (23, 29), allowing to achieve sequentially the purge of the chamber, of the capillary and of the enclosure, then the introduction of the analyte into the enclosure, and, finally, its analysis, the device being characterized by the fact that the programmer (15) is set up in such a way that:

in a first phase (51, 52), the valves of the second inlet (23) and the outlet (29) are open to let the purge gas go through, as long as a significant number of analyte particles previously analyzed may remain in the chamber (16), the enclosure (21a) or the capillary (22), in a second phase (53), the inlet valve (23) is closed, preventing the penetration of the purge gas, in a third phase (54), the transfer system (35, 32, 63, 64) is activated, to introduce the analyte to measure into the chamber (16), in a fourth phase (55), the outlet valve (29) is closed, in a fifth phase (56), at least, the analysis apparatus (2) defines the characteristics of the analyte passing from said chamber (16) into the enclosure (21a), and in a sixth phase (57), the operation starts again at the first phase, as long as there are still other products to qualify.

2. Device according to claim 1, characterized by the fact that the measuring apparatus (2) comprises a mass spectrometer (21) connected to said chamber (16) with said capillary (22).

3. Device according to claim 2, characterized by the fact that the spectrometer (21) is chosen to be able to characterize ions whose molar mass is lower or equal to 300.

4. Device according to claim 1, characterized by the fact that the transfer system is realized with a syringe (35) fitted with a needle (37) and that the gastight cap is realized with a septum (27).

5. Device according to claim 1, characterized by the fact that the transfer system comprises an adsorbing material (63) on which said analyte is adsorbed.

6. Device according to claim 5, characterized by the fact that said gastight cap is realized with removable lid (60) fitted with a tightness seam (62) and a device (66) to open and close said lid (60), to allow the introduction and extraction of said adsorbing material (63).

7. Device according to claim 6, characterized by the fact that said adsorbing material (63) is active carbon.

8. Device according to claim 1, characterized by the fact that said analysis device (21) is switched on when the purge gas penetrates into said chamber (16) and that the programmer (15) is set up in such a way that the inlet valve (23) is closed when the analysis circuit (21b) informs said programmer (15) of the disposing of the analyte previously analyzed in the gas penetrating the enclosure (21a).

9. Device according to claim 1, characterized by the fact that the outlet valve (29) is realized with a valve that lets the gas go out the chamber (16) when the pressure in it is higher than the one present beyond said valve (29).

10. Device according to claim 1, characterized by the fact that it comprises furthermore a vacuum pump (24) connected to said chamber (16) and that the programmer (15) is set up in such a way that, after the inlet valve (23) has been closed and before the transfer system is activated, said pump (24) empties the chamber (16) of the purge gas.

11. Device to qualify products containing volatile substances forming together an analyte, comprising a measuring apparatus (2) with a measuring enclosure (21a) and an analysis electronic circuit (21b) to define the characteristics of said analyte, a pumping system (30) to make a vacuum inside said enclosure (21a), a sampling chamber (16) into which said analyte is introduced and a capillary (22) to connect said chamber (16) to said enclosure (21a), said chamber (16) comprising:

a first inlet (18) to introduce said analyte and fitted with a gastight cap (27; 60, 62), a second inlet (17) connected to a source of purge gas (11) and fitted with a valve (23), and, an outlet (19) allowing the exhaust of the gas contained in said chamber (16) and also fitted with a valve (29), the device comprising furthermore a transfer system (35, 32, 63, 64) to introduce the analyte into the sampling chamber, and a command programmer (15) for the analysis circuit (21b), for the transfer system (35, 32, 63, 64) and those valves (23, 29), allowing to achieve sequentially the purge of the chamber, the capillary and the enclosure, then the introduction of the analyte into the enclosure, and, finally, its analysis, the device being characterized by the fact that the transfer system comprises an adsorbing material (63) on which the analyte is adsorbed.

12. Device according to claim 11, characterized by the fact that the programmer (15) is set up in such a way that:

in a first phase (51, 52), the valves of the second inlet (23) and the outlet (29) are open to let the purge gas go through, as long as a significant number of analyte particles previously analyzed may remain in the chamber (16), the enclosure (21a) or the capillary (22), in a second phase (53), the inlet (23) and outlet (29) valves are closed quite simultaneously, preventing particularly the penetration of purge gas, in a third phase (54), the transfer system (35, 32, 63, 64) is activated, to introduce the analyte to measure into the chamber (16), in a fourth phase, at least, the analysis apparatus (2) defines characteristics of the analyte passing from said chamber (16) into said enclosure (21a), and in a fifth phase (57), the operation starts again at the first phase, as long as there are still other products to qualify.

* * * * *